(12) United States Patent
Hamaguchi et al.

(10) Patent No.: US 7,878,194 B2
(45) Date of Patent: Feb. 1, 2011

(54) INHALER

(75) Inventors: Takehiro Hamaguchi, Ise (JP); Makoto Tabata, Kyoto (JP); Satoshi Kurata, Kyoto (JP); Yoshihiro Nakatsuji, Uji (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 907 days.

(21) Appl. No.: 11/792,591

(22) PCT Filed: Mar. 10, 2006

(86) PCT No.: PCT/JP2006/304695

§ 371 (c)(1),
(2), (4) Date: Jun. 8, 2007

(87) PCT Pub. No.: WO2006/100934

PCT Pub. Date: Sep. 28, 2006

(65) Prior Publication Data

US 2008/0083409 A1 Apr. 10, 2008

(30) Foreign Application Priority Data

Mar. 18, 2005 (JP) .............................. 2005-079991

(51) Int. Cl.
*A61M 11/00* (2006.01)
*A61M 16/00* (2006.01)
*A62B 18/02* (2006.01)
*F15B 13/00* (2006.01)
*F16K 27/04* (2006.01)

(52) U.S. Cl. ........................... 128/200.21; 128/200.14; 128/200.18; 128/203.12; 128/204.18; 128/205.24; 137/269; 137/270

(58) Field of Classification Search ..................
128/200.14–200.21, 200.24–200.25, 201.28,
128/203.11–203.13, 203.25, 204.14, 204.18,
128/204.23, 204.25, 205.11, 205.24–205.25,
128/206.21, 207.12, 207.16; 137/269, 270,
137/601.21; 239/338

See application file for complete search history.

(56) References Cited

U.S. PATENT DOCUMENTS 4,040,428 A * 8/1977 Clifford .................. 128/207.16
(Continued)

FOREIGN PATENT DOCUMENTS

CA 2244707 2/1999
(Continued)

OTHER PUBLICATIONS

Russian Office Action, mailed Dec. 4, 2008, mailed to corresponding Russian Patent Application No. 2007138564/14(042183); 7 pages.

*Primary Examiner*—Steven O Douglas
*Assistant Examiner*—Rachel T Young
(74) *Attorney, Agent, or Firm*—Morrison & Foerster LLP

(57) ABSTRACT

An inhaler has a cap body for defining a flow path and having first and second air inhalation openings for introducing outside air into the flow path from the outside; an air inhalation valve for opening and closing the first air inhalation opening by using the difference in pressure between the flow path and the outside; and a shielding section capable of selectively shielding either of the first and second air inhalation openings. The inhaler is configured to be switchable between two states that are a first state where the second air inhalation opening is shielded by the shielding section and outside air can be introduced through the first air inhalation opening by using the pressure difference and a second state where the first air inhalation opening is shielded by the shielding section and communication between the flow path and the outside through the second air inhalation opening is constantly maintained.

4 Claims, 13 Drawing Sheets

U.S. PATENT DOCUMENTS

| | | | |
|---|---|---|---|
| 4,325,366 A * | 4/1982 | Tabor | 128/207.16 |
| 4,770,413 A * | 9/1988 | Green | 482/13 |
| 5,497,944 A | 3/1996 | Weston et al. | |
| 6,176,237 B1 | 1/2001 | Wunderlich et al. | |
| 6,439,233 B1 * | 8/2002 | Geertsema | 128/207.16 |
| 2001/0042546 A1 | 11/2001 | Umeda et al. | |
| 2004/0173209 A1 | 9/2004 | Grychowski et al. | |

FOREIGN PATENT DOCUMENTS

| | | |
|---|---|---|
| EP | 0 895 788 | 2/1999 |
| EP | 1227856 A1 | 8/2002 |
| JP | 9-24097 | 1/1997 |
| JP | 11-137688 | 5/1999 |
| JP | 2001-299916 | 10/2001 |
| JP | 2003-513719 | 4/2003 |
| RU | 2 104 048 C1 | 2/1998 |
| RU | 2 188 041 C2 | 8/2002 |
| WO | WO 01/34232 A1 | 5/2001 |
| WO | WO-01/34232 A1 | 5/2001 |

\* cited by examiner

INHALER

TECHNICAL FIELD

The present invention relates to an inhaler in which liquid reserved in a reservoir portion is atomized at an atomizing portion, and generated aerosol is conveyed to oral cavity or nasal cavity of a user using a mouthpiece or the like.

BACKGROUND ART

An inhaler is a device mainly used for sterilization or treatment of bronchial tube, including an atomizing portion atomizing liquid and a conveying portion such as a mouthpiece for conveying the atomized liquid, allowing intake of the aerosol generated at the atomizing portion through one's mouth or nose, using the conveying portion such as the mouthpiece. Of these devices, inhaler in which medical liquid is turned to aerosol and conveyed for treatment is particularly referred to as an inhalation treatment device.

Generally, this type of inhaler has an air inhalation valve provided on the body of the device, so as to allow more efficient inhalation of aerosol without putting a burden on the user. The air inhalation valve is formed as a check valve attached to a wall of a flow path, so as to close a communicating hole provided on the wall of flow path forming a passage of air flow provided in the device. The air inhalation valve is for taking outer air into the flow path from the outside of the device, so that the user inhales air containing aerosol dispersed in the flow path.

A structure of the air inhalation valve is known, for example, from the disclosure of Japanese Patent Laying-Open No. 11-137688. According to the disclosure of Japanese Patent Laying-Open No. 11-137688, the air inhalation valve formed of an elastic member is attached on a lower surface of a cap body with an air inhalation opening, so that motion of the air inhalation valve is limited, to prevent excessive inhalation of the aerosol.

Patent Document 1: Japanese Patent Laying-Open No. 11-137688

DISCLOSURE OF THE INVENTION

Problems to be Solved by the Invention

When the structure disclosed in Patent Document 1 described above is adopted, it follows that the air inhalation valve as a check valve is always attached on the device, and therefore, when a user having difficulty in spontaneous intake of sufficient amount of aerosol (such as a child of relatively small vital capacity or a patient suffering from some bronchial disease), the air inhalation valve would not open sufficiently, and it would be difficult to inhale the necessary amount of aerosol. As a result, sufficient amount of aerosol would not be nebulized to the oral or nasal cavity, and the intended purpose of inhaler such as the effect of sterilization or treatment would not sufficiently be fulfilled.

When a structure in which the air inhalation valve is not provided and only an air inhalation opening is provided on the wall of a flow path is adopted, though inhalation of aerosol becomes easier for a person having difficulty in spontaneous intake of sufficient amount of aerosol, a person having relatively large vital capacity (such as an adult male) would inhale excessively, and inhalation of an appropriate amount of aerosol becomes difficult.

In view of the foregoing, a structure having a detachable air inhalation valve may be possible. Such a structure, however, requires repeated operations of attachment and detachment for use, so that the air inhalation valve may be damaged or lost. Further, the operations of attachment and detachment are very troublesome, putting a burden on the user.

Therefore, the present invention was made to solve the above-described problems and its object is to provide an inhaler allowing switching between presence and absence of the air inhalation valve by a very simple operation.

Means for Solving the Problems

According to a first aspect, the present invention provides an inhaler, including: a flow path wall defining a flow path through which airflow moves, having first and second air inhalation openings for introducing external air from outside to the flow path; an atomizing portion provided in the flow path, for atomizing liquid reserved in a reservoir; a conveying portion conveying an air flow containing aerosol generated at the atomizing portion to the outside; an air inhalation valve attached to the flow path wall at a portion where the first air inhalation opening is provided, for opening/closing the first air inhalation opening utilizing pressure difference between the flow path and the outside; and a shielding section capable of selectively shielding either one of the first and second air inhalation openings; wherein the inhaler is structured switchable between a first state in which the second air inhalation opening is closed by the shielding section allowing introduction of external air through the first air inhalation opening utilizing the pressure difference, and a second state in which the first air inhalation opening is closed by the shielding section and communication between the flow path and the outside through the second air inhalation opening is always maintained.

In the inhaler according to the first aspect of the present invention described above, the inhaler may have a case body including the flow path wall of portions not provided with the first and second air inhalation openings, and a cap body including the flow path wall of portions provided with the first and second air inhalation openings, and it may be formed by attaching the cap body to the case body. In that case, the shielding portion is preferably formed by the flow path wall of the portion provided on the case body; and it is preferably structured such that switching between the first state and the second state is made possible by changing relative position of attachment of the cap body to the case body.

In the inhaler according to the first aspect of the present invention described above, the shielding section is preferably formed by a slider attached slidably on a surface of the flow path wall; and it is preferably structured such that switching between the first state and the second state is made possible by changing relative position of the slider on the surface of the flow path wall by moving the slider.

In the inhaler according to the first aspect of the present invention described above, the shielding section is preferably formed by a rotating plate attached on a surface of the flow path wall, rotatably about a rotating shaft arranged in a direction parallel to the surface; and it is preferably structured such that switching between the first state and the second state is made possible by changing relative position of the rotating plate on the surface of the flow path wall by rotating the rotating plate.

According to a second aspect, the present invention provides an inhaler, including: a flow path wall defining a flow path through which airflow moves, having an air inhalation opening for introducing external air from outside to the flow path; an atomizing portion provided in the flow path, for atomizing liquid reserved in a reservoir; a conveying portion conveying an air flow containing aerosol generated at the atomizing portion to the outside; an air inhalation valve formed to be capable of opening/closing the air inhalation opening utilizing pressure difference between the flow path and the outside; and a position changing means for selectively changing relative position of arrangement of the air inhalation valve in the flow path; wherein the inhaler is structured switchable between a first state in which the air inhalation valve is arranged at a position allowing opening/closing of the air inhalation opening utilizing the pressure difference, and a second state in which the air inhalation valve is arranged at a position not allowing opening/closing of the air inhalation opening utilizing the pressure difference and communication between the flow path and the outside through the air inhalation opening is always maintained.

In the inhaler according to the second aspect of the present invention, the position changing means is preferably formed by a rod having one end fixed to the air inhalation valve and the other end movably supported by the flow path wall; and it is preferably structured such that switching between the first state and the second state is made possible by changing position of the rod relative to the flow path wall.

Effects of the Invention

According to the present invention, presence/absence of the air inhalation valve can be switched by a very simple operation, and therefore, nebulizing of an appropriate amount of aerosol can be realized without posing a burden on the user.

DESCRIPTION OF THE REFERENCE SIGNS 1 inhaler, 10 compressor, 20 tube, 100A~100D nebulizer, 101 flow path, 110 case body, 112 connecting portion, 114 compressed air introducing tube, 116 reservoir, 117 cut out portion, 118 alignment mark, 120 atomizing portion forming body, 122 baffle, 124 liquid suction tube forming portion, 130 flow path forming body, 132 shielding section forming wall, 140 air inhalation valve, 142 attachment portion, 150 cap body, 152 air inhalation opening, 152a first air inhalation opening, 152b second air inhalation opening, 154 partition wall, 157 projection, 158 alignment mark, 160 mouthpiece, 170 exhalation valve, 180 fixing member, 191 slider, 192 rotating plate, 192a shaft portion, 193 rod, 193a support portion, 200 liquid.

BEST MODES FOR CARRYING OUT THE INVENTION

In the following, embodiments of the present invention will be described in detail with reference to the figures. In the embodiments described below, a compressor type inhaler will be described as an exemplary inhaler.

Embodiment 1

Figure 1:
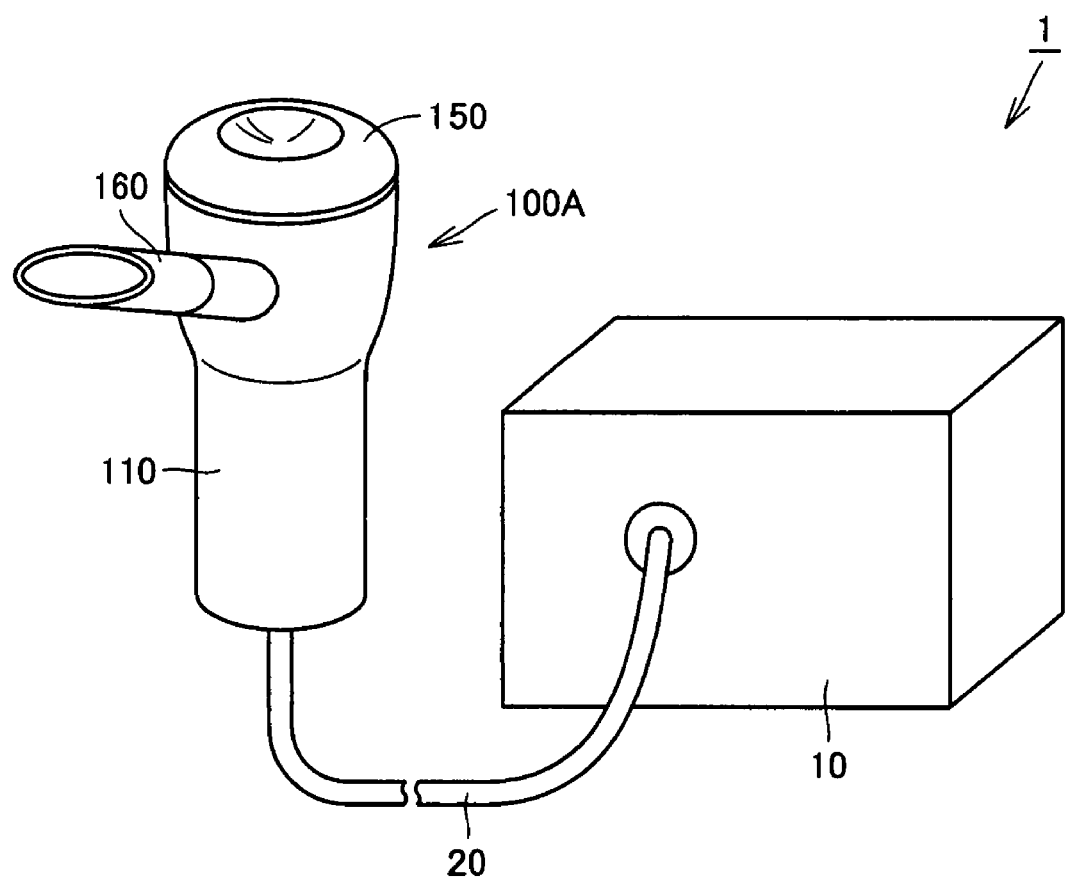
FIG. 1 is an external view showing device structure of the inhaler in accordance with Embodiment 1 of the present invention.
Figure 2:
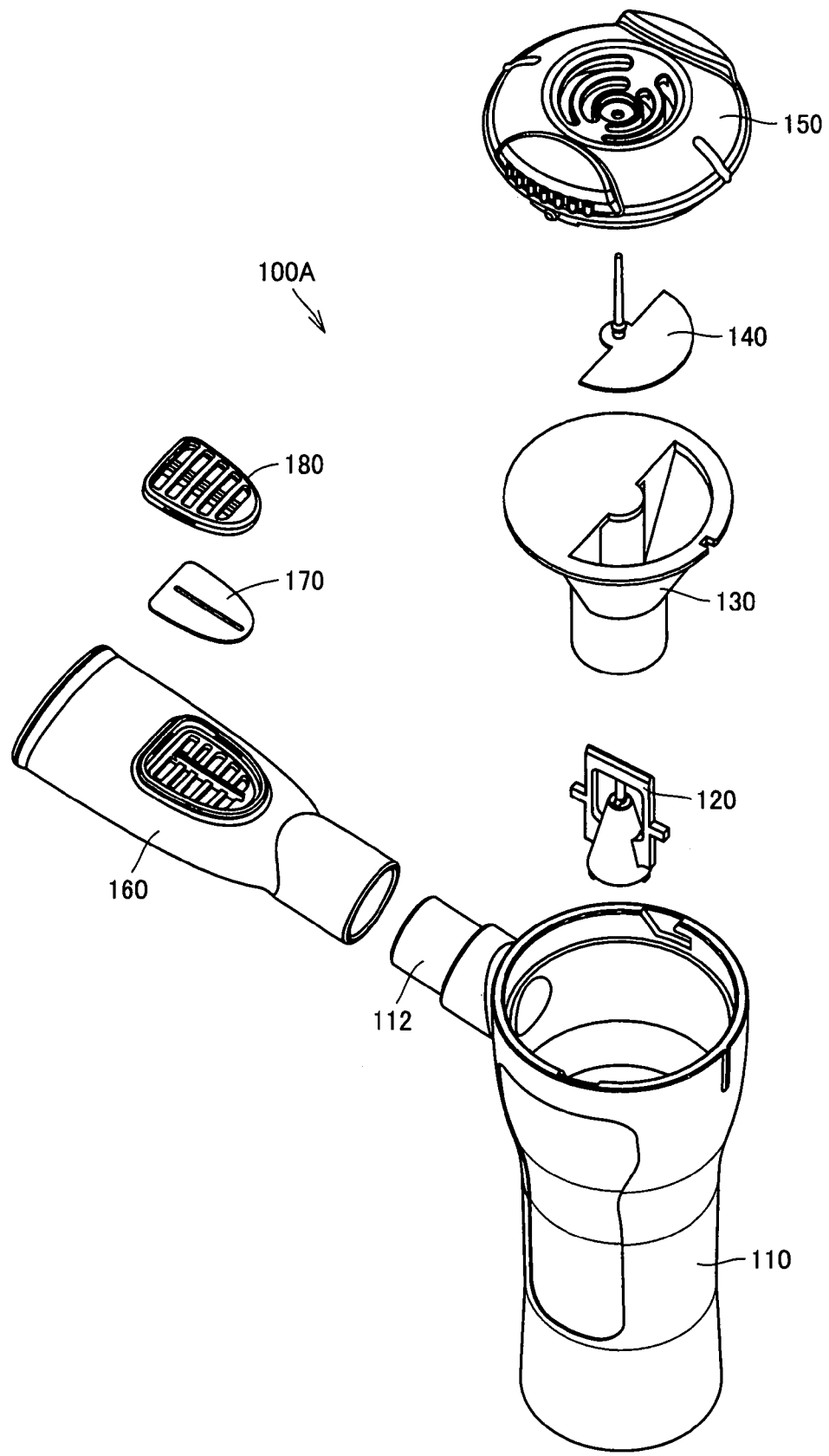
FIG. 2 is an exploded perspective view showing assembly of a nebulizer of the inhaler shown in FIG. 1.
Figure 3A:
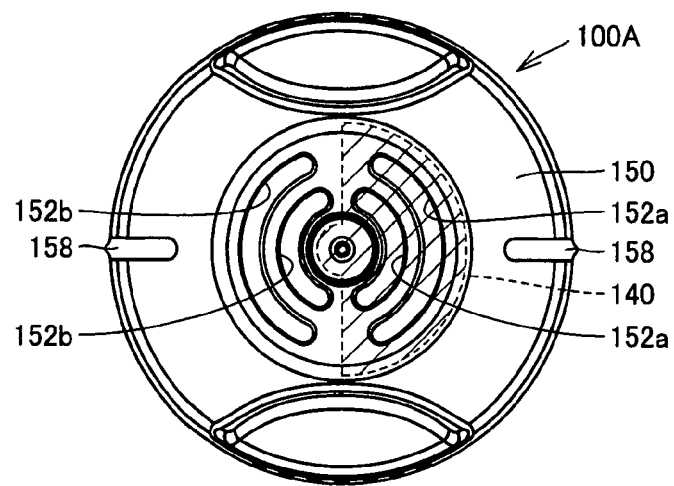
FIG. 3A is a top view of a first state in which the air inhalation valve is functionable after assembly of the nebulizer shown in FIG. 2.
Figure 3B:
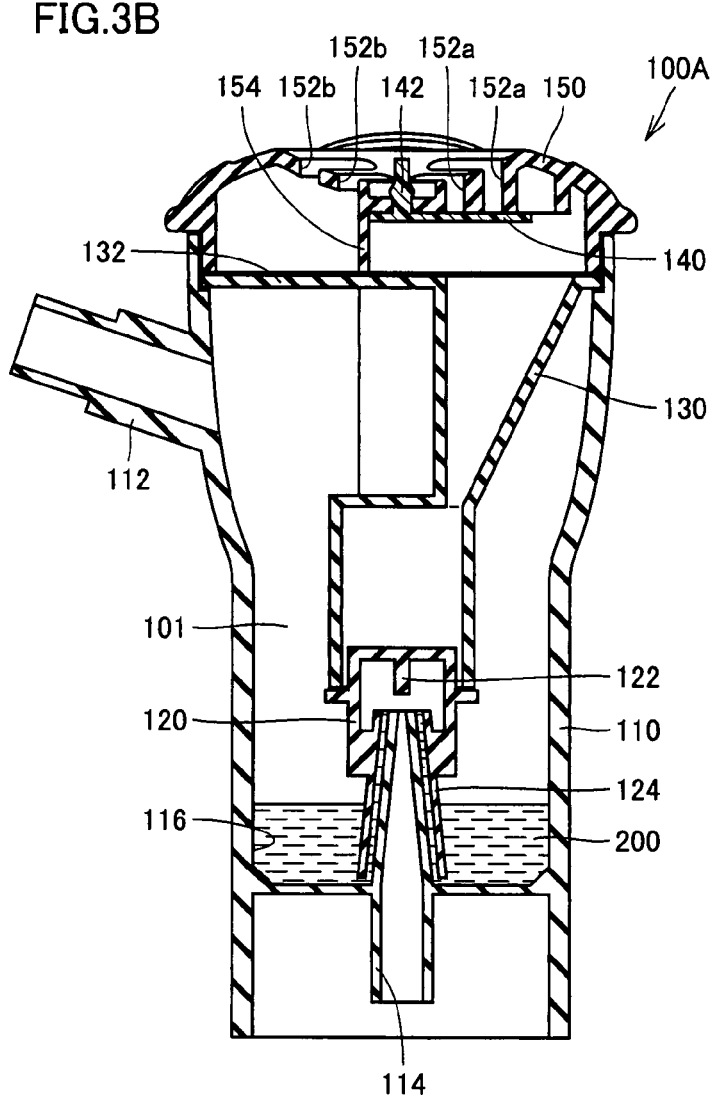
FIG. 3B is a cross-sectional view of the first state in which the air inhalation valve is functionable after assembly of the nebulizer shown in FIG. 2.
Figure 4A:
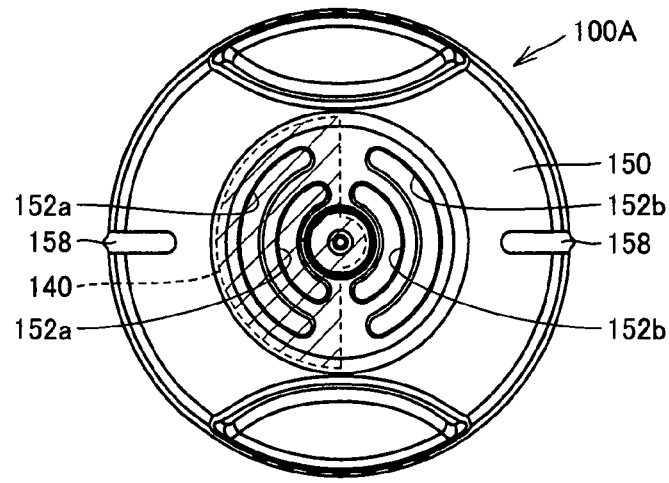
FIG. 4A is a top view of a second state in which the air inhalation valve is unfunctionable after assembly of the nebulizer shown in FIG. 2.
Figure 4B:
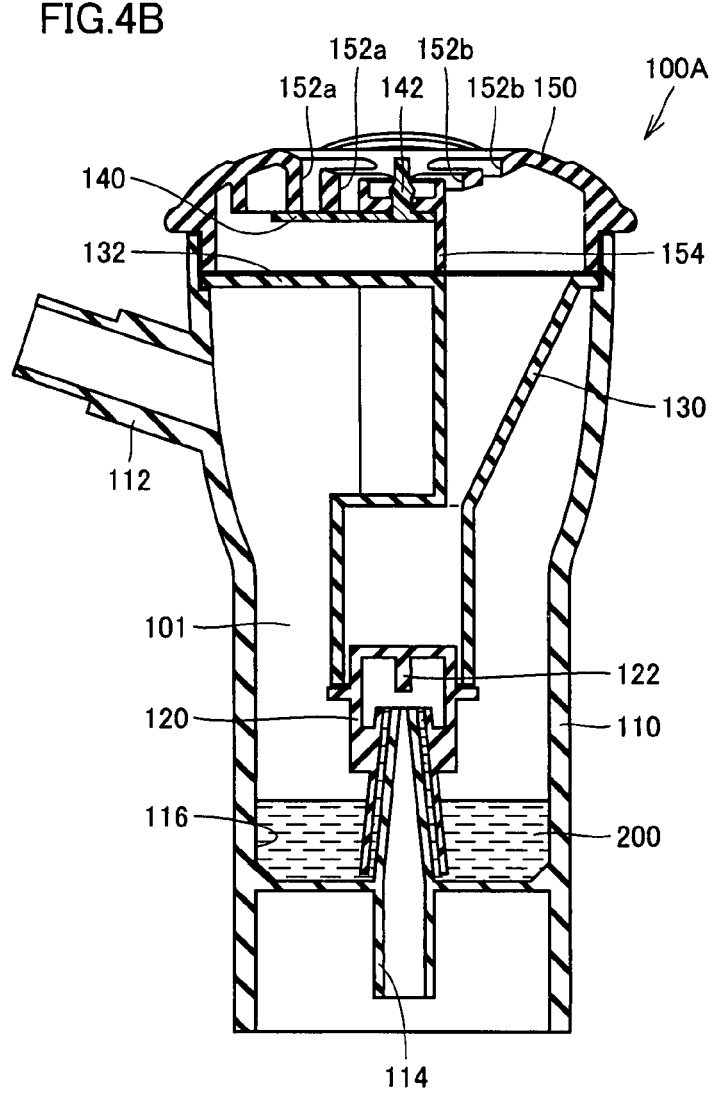
FIG. 4B is a cross-sectional view of the second state in which the air inhalation valve is unfunctionable after assembly of the nebulizer shown in FIG. 2.

FIG. 1 is an external view showing device structure of the inhaler in accordance with Embodiment 1 of the present invention. FIG. 2 is an exploded perspective view showing assembly of a nebulizer of the inhaler shown in FIG. 1. FIGS. 3A and 3B are top view and cross-sectional view, respectively, of a first state in which the air inhalation valve is functionable after assembly of the nebulizer shown in FIG. 2, and FIGS. 4A and 4B are a top view and a cross-sectional view, respectively, of a second state in which the air inhalation valve is unfunctionable after assembly of the nebulizer shown in FIG. 2. In FIGS. 3A, 3B, 4A and 4B, the mouthpiece shown in FIG. 2 is not shown.

As shown in FIG. 1, an inhaler 1 in accordance with the present embodiment includes a compressor 10, a tube 20 and a nebulizer 100A. Compressor 10 feeds pressurized compressed air to nebulizer 100A through tube 20.

As shown in FIGS. 2, 3A, 3B, 4A and 4B, nebulizer 100A includes a case body 110, an atomizing portion forming body 120, a flow path forming body 130, an air inhalation valve 140 and a cap body 150. Case body 110 has an approximately cylindrical shape, and atomizing portion forming body 120 and flow path forming body 130 are contained and arranged in case body 110. Air inhalation valve 140 is attached to a lower surface of cap body 150, and cap body 150 is attached to case body 110 to close an opening provided at an upper end of case body 110.

Case body 110 has a connecting portion 112 at a prescribed position on its circumferential surface, and a mouthpiece 160 is connected to connecting portion 112. As shown in FIG. 2, an exhalation valve 170 and a fixing member 180 allowing fixation of exhalation valve 170 on mouthpiece 160 are attached to the mouthpiece 160.

As shown in FIGS. 3B and 4B, on a bottom surface of case body 110, a compressed air introducing tube 114 is arranged to extend in upward/downward direction. To a lower tip end of compressed air introducing tube 114, tube 20 described above is attached. Thus, the compressed air generated by compressor 10 is introduced to compressed air introducing tube 114 through tube 20. An upper tip end of compressed air introducing tube 114 is formed in a tapered shape, and facing a baffle 122 provided on an atomizing portion forming body 120, which will be described later. Further, a reservoir 116 is provided around that portion of case body 110 at which the compressed air introducing tube 114 is formed. Reservoir 116 is a portion for temporarily reserving liquid 200 such as water, saline or medical solution.

A liquid suction tube forming portion 124 of atomizing portion forming body 120 is arranged, facing from above compressed air introducing tube 114. An inner wall surface of liquid suction tube forming portion 124 is arranged positioned at a prescribed distance from an outer wall surface of compressed air introducing tube 114, with its lower end arranged to extend close to the bottom surface of reservoir 116 described above. A space between liquid suction tube forming portion 124 and compressed air introducing tube 114 forms a liquid suction tube, and by capillary action, liquid 200 reserved in reservoir 116 is sucked up close to the atomizing portion, which will be described later.

As described above, baffle 122 of atomizing portion forming body 120 is arranged facing the upper tip end portion of compressed air introducing tube 114, and this portion forms the atomizing portion. At the atomizing portion, compressed air introduced to compressed air introducing tube 114 by compressor 10 is ejected from the upper tip end portion of compressed air introducing tube 114 to baffle 122. At this time, liquid 200 that has been sucked by capillary action close to the atomizing portion is blown up by negative pressure generated at the atomizing portion, and nebulized, together with the compressed air, toward baffle 122. Because of this function, liquid 200 impinges on baffle 122 to be fine droplets, and the fine droplets are dispersed in the air flowing through flow path 101 to be the aerosol.

A flow path forming body 130 is arranged positioned above atomizing portion forming body 120, and by flow path forming body 130, flow path 101 through which air flows is formed inside case body 110. Flow path 101 is communicated to the above-described connecting portion 112 formed at the circumferential surface of case 110, and through this connecting portion 112, the aerosol generated by the atomizing portion is introduced to mouthpiece 160. At an upper end portion of flow path forming body 130, a shielding section forming wall 132 to be a part of a shielding portion, which will be described later, is provided.

As shown in FIGS. 3A, 3B, 4A and 4B, a first air inhalation opening 152a and a second air inhalation opening 152b are provided at prescribed positions of the above-described cap body 150. Cap body 150 has an approximately circular outer shape when viewed from above, and assuming that cap body 150 is divided into left and right two sides, the first air inhalation opening 152a is formed on one side and the second air inhalation opening 152b is formed on the other side. Further, at a lower surface of cap body 150 at a portion positioned between the first and second air inhalation openings 152a and 152b, a partition wall 154 is formed protruding downward. Partition wall 154 reaches an upper end surface of the above-described flow path forming body 130, and is in contact with shielding section forming wall 132 of flow path forming body 130.

On a lower surface of cap body 150, an air inhalation valve 140 is attached. Air inhalation valve 140 has an approximately semi-circular shape, and it is arranged adjacent to the partition wall 154 to close the first air inhalation opening 152a. Air inhalation valve 140 is attached to cap body 150 by inserting an attachment portion 142 provided on air inhalation valve 140 into an opening formed in cap body 150. The air inhalation valve 140 is a check valve, formed of highly flexible rubber or resin such as silicone or elastomer, for opening/closing the first air inhalation opening 152a utilizing pressure difference between the inner pressure of flow path 101 and pressure outside the nebulizer 100A. Specifically, air inhalation valve 140 is for taking external air from nebulizer 100A to flow path 101, so as to allow the user to inhale air containing aerosol dispersed in flow path 101.

In the first state shown in FIGS. 3A and 3B, the second air inhalation opening 152b is in a state shielded by shielding section forming wall 132 and partition wall 154 as the shielding section, and the second air inhalation opening 152b is not communicated with flow path 101. On the other hand, the first air inhalation opening 152a is communicated with flow path 101 through air inhalation valve 140. Therefore, air inhalation valve 140 is in a state capable of opening/closing the first air inhalation opening 152a utilizing pressure difference between the inner pressure of flow path 101 and the pressure outside the nebulizer 100A, and when the user inhales the aerosol, flow path 101 comes to have negative pressure and air inhalation valve 140 is pressed downward, whereby flow path 101 is communicated with the outside of nebulizer 100A. Therefore, because of the negative pressure, the external air comes to be introduced through the first air inhalation opening 152*a* to flow path 101. When the user exhales a breath to flow path 101, inner pressure of flow path 101 increases, and hence, air inhalation valve 140 is pressed to the lower surface of cap body 150, and the first air inhalation opening 152*a* comes to be in a closed state. The first state shown in FIGS. 3A and 3B is suitable for use by a user with large inhalation capacity who can inhale aerosol relatively easily.

In the second state shown in FIGS. 4A and 4B, the first air inhalation opening 152*a* is in a state shielded by shielding section forming wall 132 and partition wall 154 as the shielding section, and the first air inhalation opening 152*a* is not communicated with flow path 101. Therefore, air inhalation valve 140 does not function as a check valve. On the other hand, the second air inhalation opening 152*b* is in a state communicated with flow path 101, and as a result, flow path 101 and the outside of nebulizer 101 are communicated through the second air inhalation opening 152*b*. Therefore, the second air inhalation opening 152*b* is always in a communicated state, and hence, when the user inhales the aerosol, flow path 101 comes to have a negative pressure and the external air is introduced through the second air inhalation opening 152*b* to flow path 101. The second state shown in FIGS. 4A and 4B is suitable for use by a user with small inhalation capacity who has relative difficulty in inhaling the aerosol.

Figure 5:
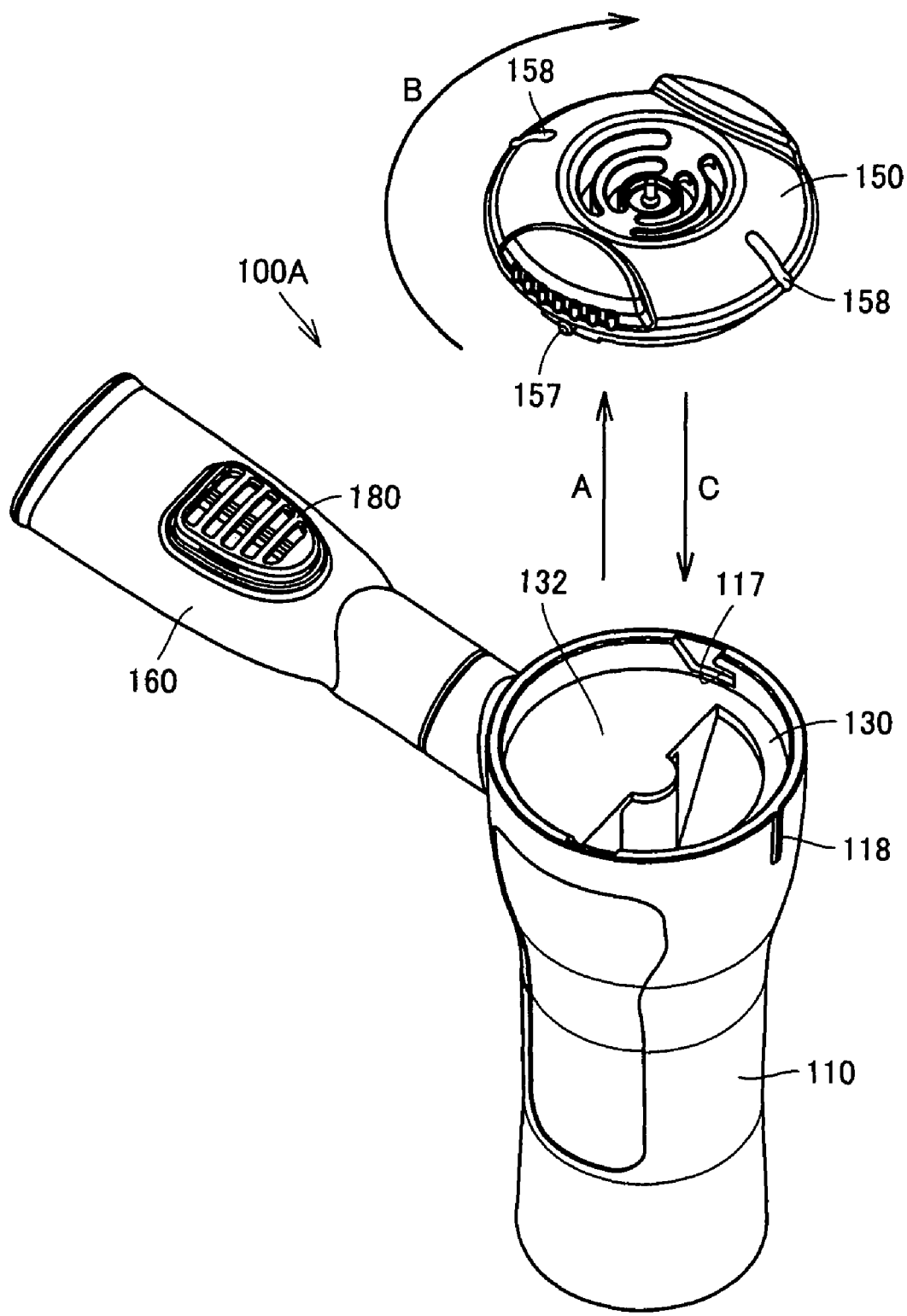
FIG. 5 illustrates a specific method of operation for switching between the first state and the second state in the inhaler in accordance with Embodiment 1 of the present invention.
Figure 6A:
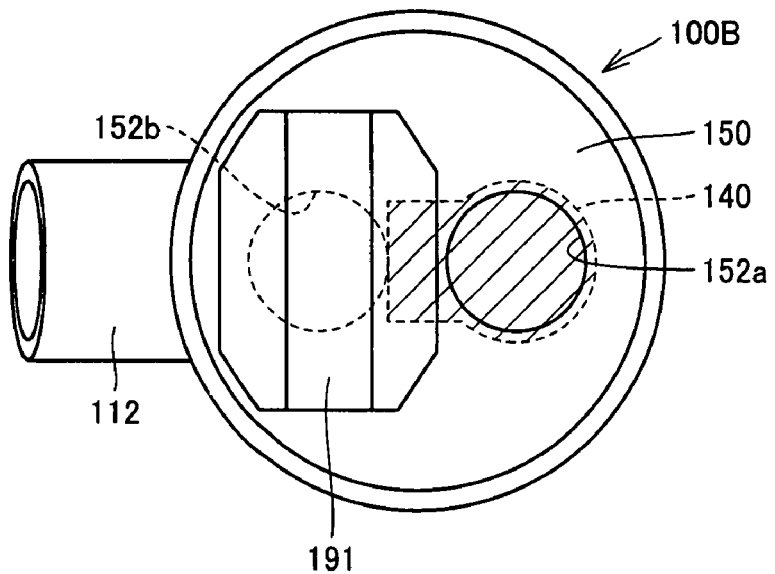
FIG. 6A is a top view of the nebulizer of the inhaler in accordance with Embodiment 2 of the present invention in the first state in which the air inhalation valve is functionable.
Figure 6B:
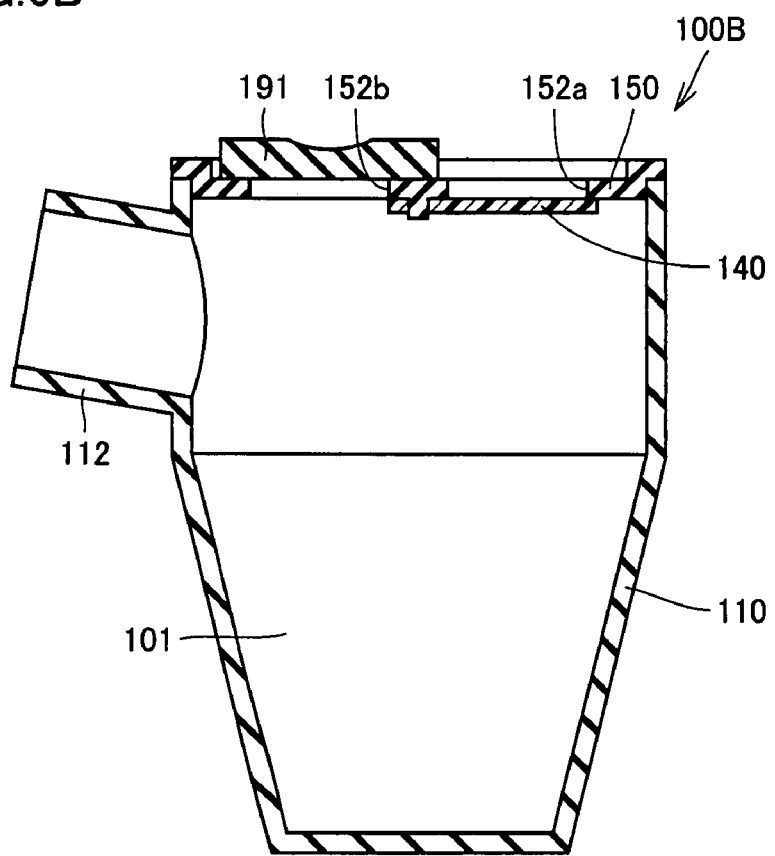
FIG. 6B is a cross-sectional view of the nebulizer of the inhaler in accordance with Embodiment 2 of the present invention in the first state in which the air inhalation valve is functionable.
Figure 7A:
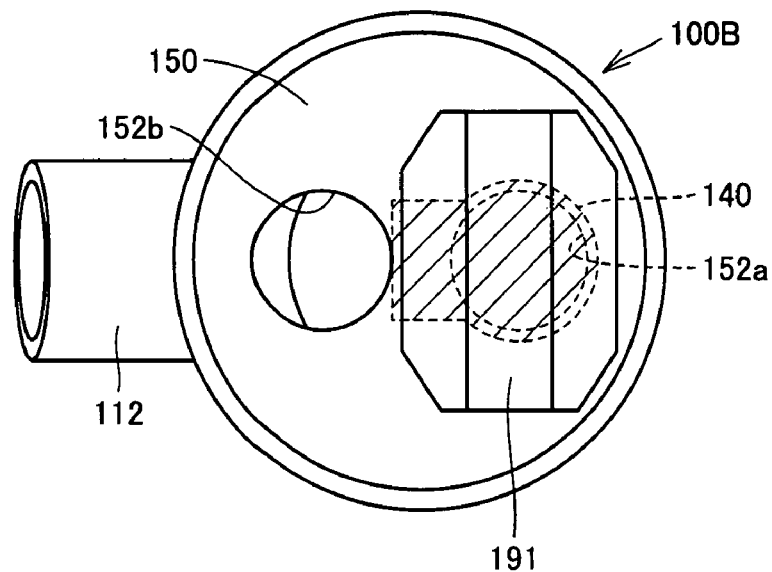
FIG. 7A is a top view of the nebulizer of the inhaler in accordance with Embodiment 2 of the present invention in the second state in which the air inhalation valve is unfunctionable.
Figure 7B:
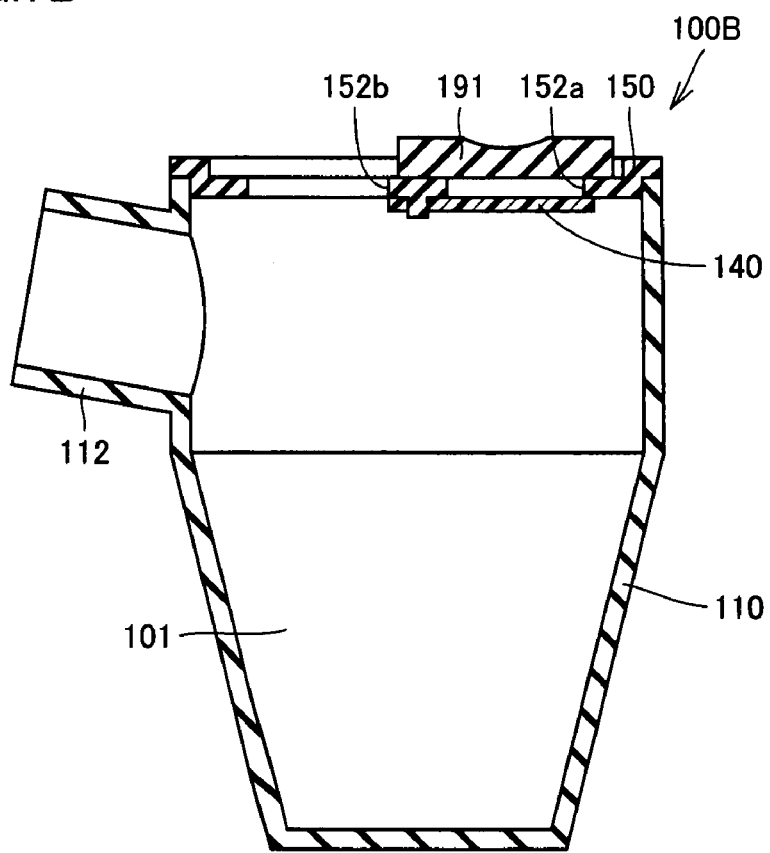
FIG. 7B is a cross-sectional view of the nebulizer of the inhaler in accordance with Embodiment 2 of the present invention in the second state in which the air inhalation valve is unfunctionable.
Figure 8A:
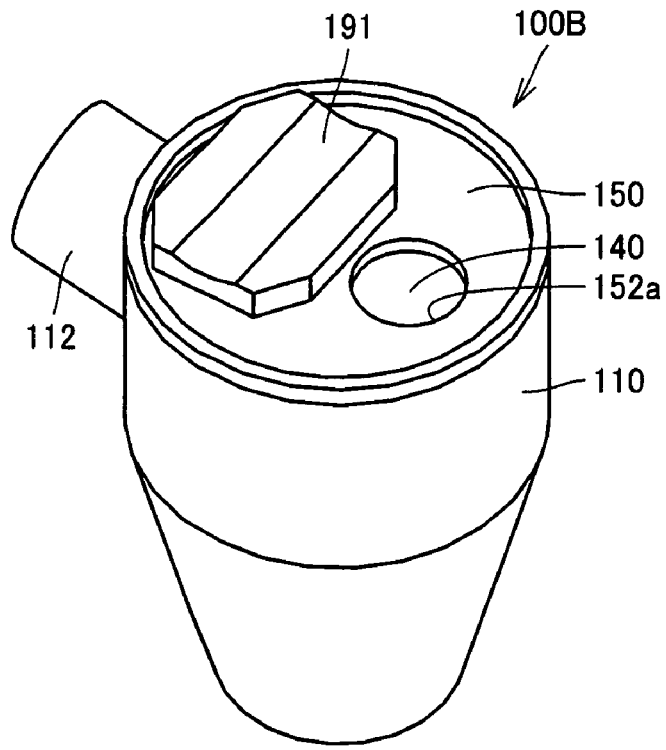
FIG. 8A is a perspective view of the nebulizer of the inhaler in accordance with Embodiment 2 of the present invention in the first state in which the air inhalation valve is functionable.
Figure 8B:
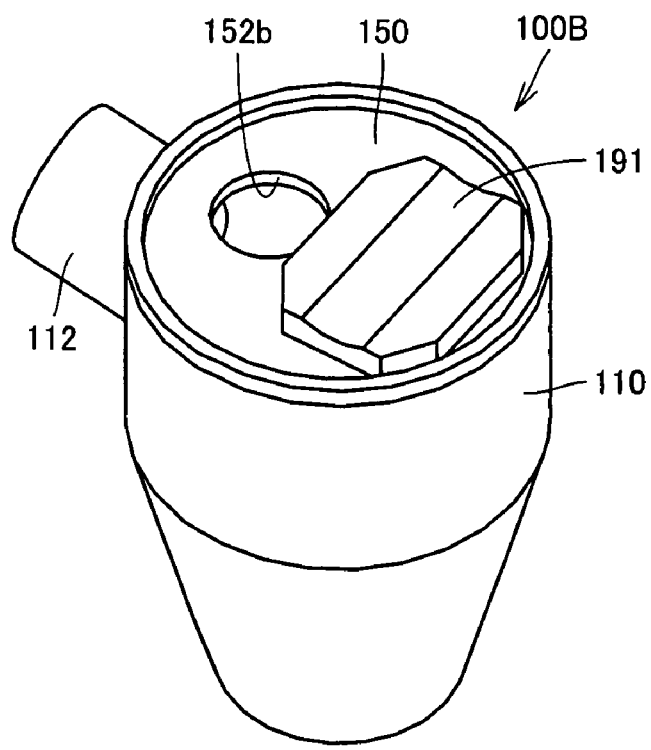
FIG. 8B is a perspective view of the nebulizer of the inhaler in accordance with Embodiment 2 of the present invention in the second state in which the air inhalation valve is unfunctionable.

FIG. 5 illustrates a specific method of operation for switching between the above-described first and second states, of the inhaler in accordance with the present embodiment. As shown in FIG. 5, in nebulizer 100A of the inhaler in accordance with the present embodiment, the above-described first and second states are switched by removing cap body 150 from case body 110 as represented by an arrow A in the figure, rotating the cap body 150 by 180° in a horizontal state as represented by an arrow B in the figure and by attaching cap body 150 to case body 110 again as represented by an arrow C in the figure. Cap body 150 is fixed to case body 110 by inserting a pair of projections 157 provided at opposite portions on a side portion of cap body 150 into cut out portions 117 provided at opposite positions on the inner circumferential surface at an upper end of case body 110. In order to facilitate positioning for insertion, alignment marks 118 and 158 are respectively provided on case body 110 and cap body 150, respectively.

By adopting the above-described structure, it becomes possible to switch presence/absence of the air inhalation valve by a very simple operation of removing the cap body once, changing its direction and attaching it again. Therefore, it becomes possible to nebulize an appropriate amount of aerosol without posing a burden on the user. Further, in order to switch presence/absence of the air inhalation valve, it is unnecessary to remove only the air inhalation valve from the device body. Therefore, the air inhalation valve may not be damaged or lost. Thus, an inhaler with good handling can be provided.

Embodiment 2

FIGS. 6A and 6B are a top view and a cross-sectional view, respectively, of the nebulizer of the inhaler in accordance with Embodiment 2 of the present invention in the first state in which the air inhalation valve is functionable, and FIGS. 7A and 7B are a top view and a cross-sectional view, respectively, of the nebulizer of the inhaler in accordance with Embodiment 2 of the present invention in the second state in which the air inhalation valve is unfunctionable. FIG. 8A is a perspective view of the nebulizer of the inhaler in accordance with Embodiment 2 of the present invention in the first state in which the air inhalation valve is functionable and FIG. 8B is a perspective view of the second state in which the air inhalation valve is unfunctionable. In FIGS. 6A, 6B, 7A, 7B, 8A and 8B, the mouthpiece is not shown, and in FIGS. 6B and 7B, internal mechanism of the nebulizer is not shown. Portions similar to those of nebulizer 100A of Embodiment 1 described above are denoted by the same reference characters in the figure, and description thereof will not be repeated here.

As shown in FIGS. 6A, 6B, 7A, 7B, 8A and 8B, in nebulizer 100B of the inhaler in accordance with the present embodiment, the first and second air inhalation openings 152*a* and 152*b* are provided at prescribed positions of cap body 150. Cap body 150 has an approximately circular outer shape when viewed from above, and assuming that cap body 150 is divided into left and right two sides, the first air inhalation opening 152*a* is formed on one side and the second air inhalation opening 152*b* is formed on the other side. On a lower surface of cap body 150, an air inhalation valve 140 is attached. Air inhalation valve 140 is formed to close the first air inhalation opening 152*a*, and it is a check valve for opening/closing the first air inhalation opening 152*a* utilizing pressure difference between the inner pressure of flow path 101 and pressure outside the nebulizer 100B.

On an outer surface of cap body 150, a slider 191 as the shielding section is provided slidably. In the first state shown in FIGS. 6A, 6B and 8A, slider 191 is arranged at a position shielding the second air inhalation opening 152*b*. Therefore, in the first state, the second inhalation opening 152*b* is in a state not communicated with the outside of nebulizer 100B. On the other hand, the first air inhalation opening 152*a* is communicated with flow path 101 through air inhalation valve 140. Therefore, air inhalation valve 140 is in a state capable of opening/closing the first air inhalation opening 152*a* utilizing pressure difference between the inner pressure of flow path 101 and the pressure outside the nebulizer 100B, and when the user inhales the aerosol, flow path 101 comes to have negative pressure and air inhalation valve 140 is pressed downward, whereby flow path 101 is communicated with the outside of nebulizer 100B. Therefore, because of the negative pressure, the external air comes to be introduced through the first air inhalation opening 152*a* to flow path 101.

In the second state shown in FIGS. 7A, 7B and 8B, slider 191 is arranged at a position shielding the first air inhalation opening 152*a*. Therefore, in the second state, the first air inhalation opening 152*a* is in a state not communicated with the outside of nebulizer 100B. Therefore, air inhalation valve 140 does not function as a check valve. On the other hand, the second air inhalation opening 152*b* is in a state communicated with the outside of nebulizer 100B, and as a result, flow path 101 is communicated with the outside of nebulizer 100B through the second air inhalation opening 152*b*. Therefore, the second air inhalation opening 152*b* is always in a communicated state, and hence, when the user inhales the aerosol, flow path 101 comes to have a negative pressure and the external air is introduced through the second air inhalation opening 152*b* to flow path 101.

By adopting the structure described above, by a very simple operation of sliding the slider on an outer surface of cap body, presence/absence of the air inhalation valve can be switched. Therefore, an appropriate amount of aerosol can be nebulized without putting a burden on the user. Further, in order to switch presence/absence of the air inhalation valve, it is unnecessary to remove only the air inhalation valve from the device body. Therefore, the air inhalation valve may not be damaged or lost. Thus, an inhaler with good handling can be provided.

As the inhaler in accordance with the present embodiment, an example having a slider as the shielding section provided on an outer surface of the cap body has been described. A structure in which the slider as the shielding section is provided inside the nebulizer is also possible. In that case, the slider as the shielding section may be arranged on an inner surface of the case body defining the flow path or on an inner surface of the cap body.

Embodiment 3

Figure 9A:
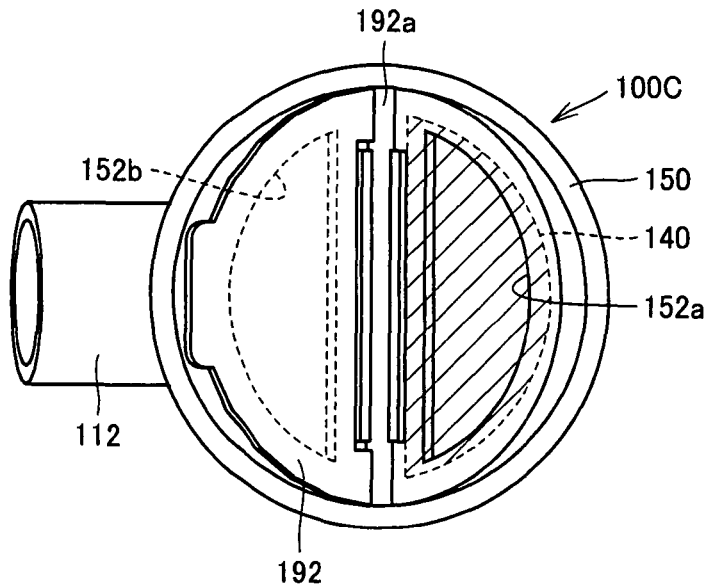
FIG. 9A is a top view of the nebulizer of the inhaler in accordance with Embodiment 3 of the present invention in the first state in which the air inhalation valve is functionable.
Figure 9B:
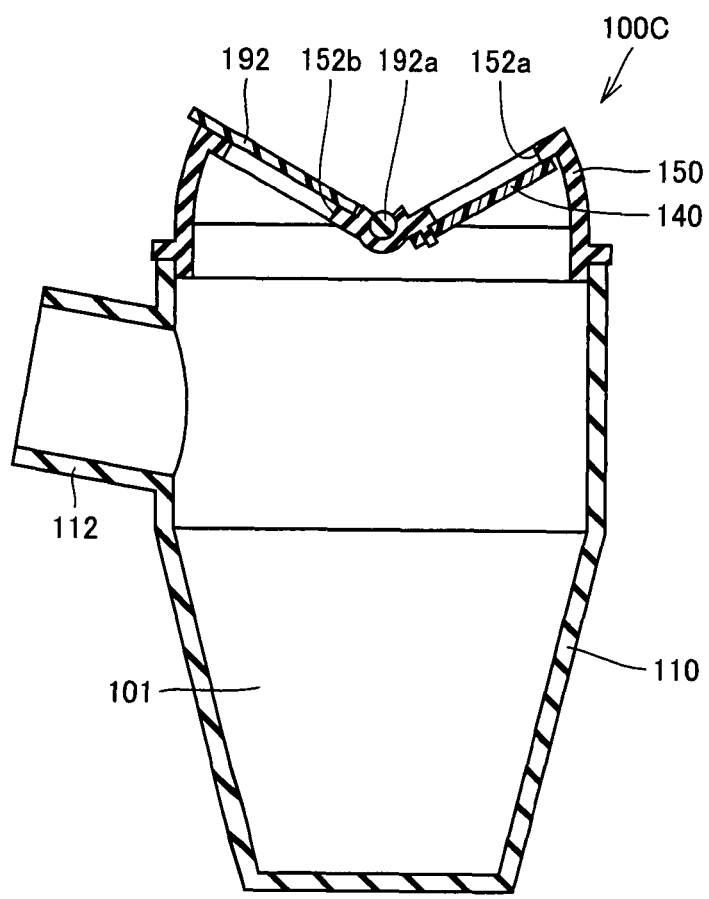
FIG. 9B is a cross-sectional view of the nebulizer of the inhaler in accordance with Embodiment 3 of the present invention in the first state in which the air inhalation valve is functionable.
Figure 10A:
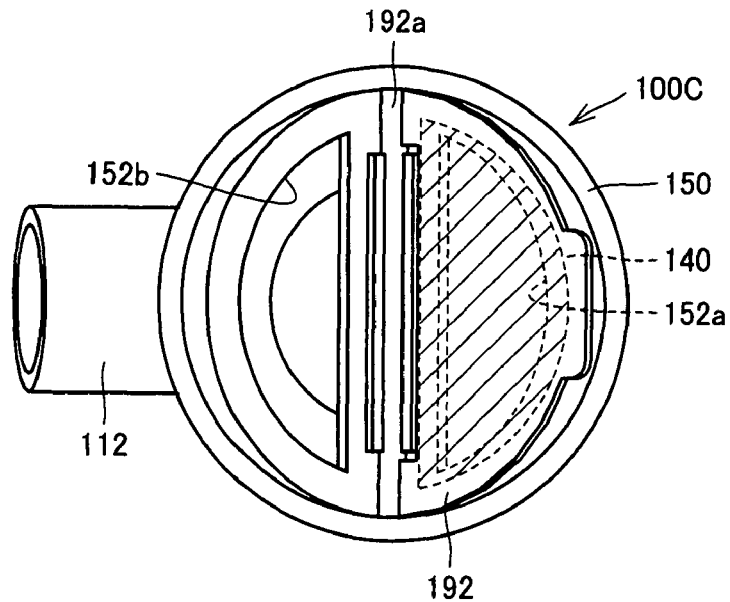
FIG. 10A is a top view of the nebulizer of the inhaler in accordance with Embodiment 3 of the present invention in the second state in which the air inhalation valve is unfunctionable.
Figure 10B:
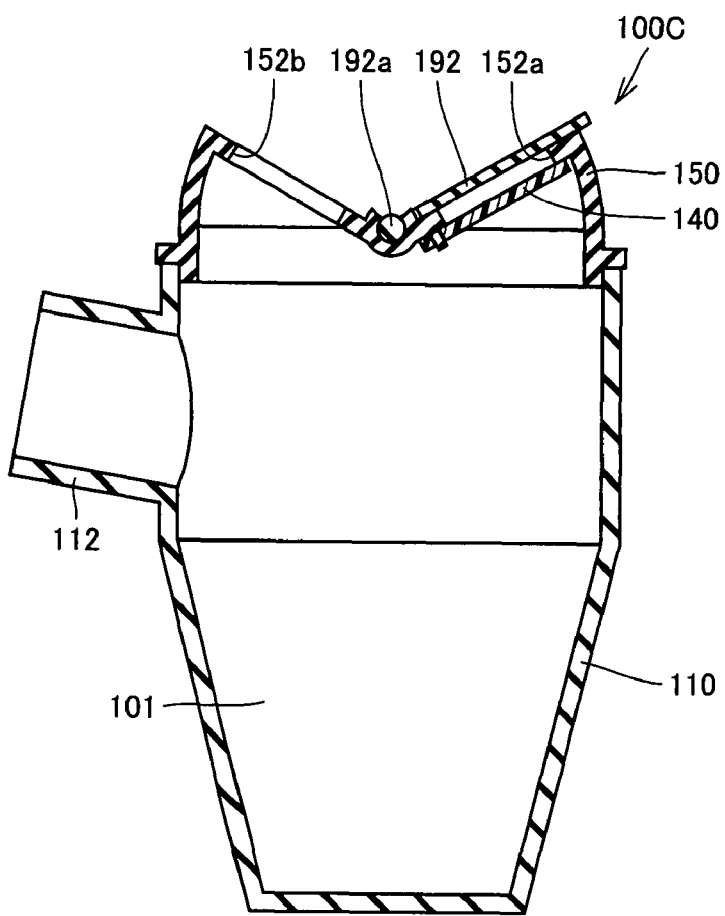
FIG. 10B is a cross-sectional view of the nebulizer of the inhaler in accordance with Embodiment 3 of the present invention in the second state in which the air inhalation valve is unfunctionable.
Figure 11A:
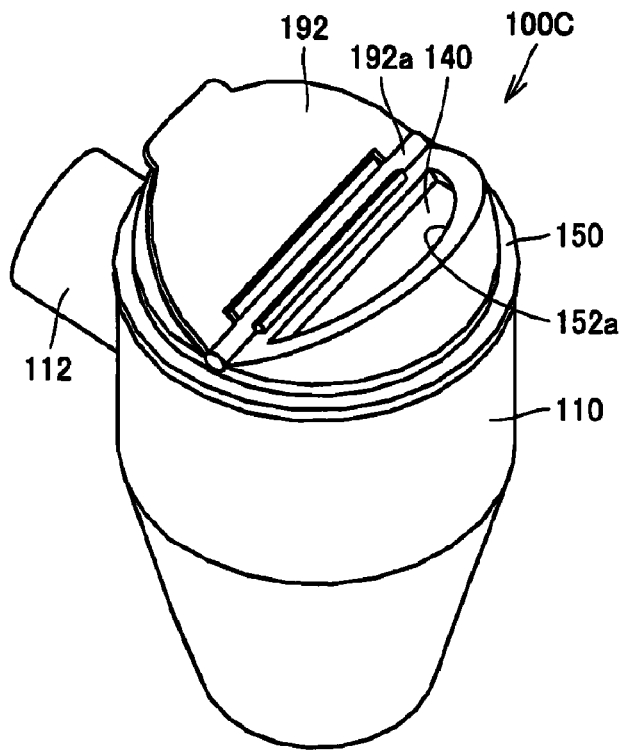
FIG. 11A is a perspective view of the nebulizer of the inhaler in accordance with Embodiment 3 of the present invention in the first state in which the air inhalation valve is functionable.
Figure 11B:
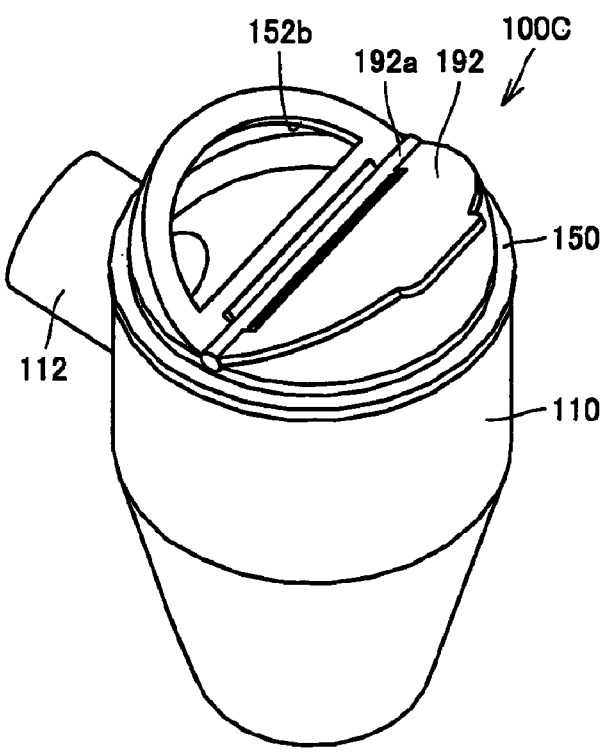
FIG. 11B is a perspective view of the nebulizer of the inhaler in accordance with Embodiment 3 of the present invention in the second state in which the air inhalation valve is unfunctionable.

FIGS. 9A and 9B are a top view and a cross-sectional view, respectively, of the nebulizer of the inhaler in accordance with Embodiment 3 of the present invention in the first state in which the air inhalation valve is functionable, and FIGS. 10A and 10B are a top view and a cross-sectional view, respectively, of the nebulizer of the inhaler in accordance with Embodiment 3 of the present invention in the second state in which the air inhalation valve is unfunctionable. FIG. 11A is a perspective view of the nebulizer of the inhaler in accordance with Embodiment 3 of the present invention in the first state in which the air inhalation valve is functionable, and FIG. 11B is a perspective view of the second state in which the air inhalation valve is unfunctionable. In FIGS. 9A, 9B, 10A, 10B, 11A and 11B, the mouthpiece is not shown, and in FIGS. 9B and 10B, internal mechanism of the nebulizer is not shown. In the figures, portions similar to those of nebulizer 100A of the inhaler in accordance with Embodiment 1 are denoted by the same reference characters, and description thereof will not be repeated here.

As shown in FIGS. 9A, 9B, 10A, 10B, 11A and 11B, cap body 150 of a nebulizer 100C of the inhaler in accordance with the present embodiment has an approximately circular outer shape when viewed from above, and its surface is formed to have a V-shaped cross section. At prescribed positions of cap body 150, the first and second air inhalation openings 152a and 152b are provided. Cap body 150 formed to have the V-shaped cross-section has its upper surface divided into left and right two sides with the bent portion in-between, the first air inhalation opening 152a is formed on one side and the second air inhalation opening 152b is formed on the other side. On a lower surface of cap body 150, an air inhalation valve 140 is attached. Air inhalation valve 140 is arranged to close the first air inhalation opening 152a, and it is a check valve for opening/closing the first air inhalation opening 152a utilizing pressure difference between the inner pressure of flow path 101 and pressure outside the nebulizer 100C.

On an outer surface of cap body 150, a rotating plate 192 as the shielding section is provided rotatably. Rotating plate 192a is formed such that its shaft portion 192a is arranged in a direction parallel to the outer surface of cap body 150, and more specifically, it is formed rotatable with the shaft portion 192a supported at the bent portion mentioned above.

In the first state shown in FIGS. 9A, 9B and 11A, rotating plate 192 is arranged at a position shielding the second air inhalation opening 152b. Therefore, in the first state, the second air inhalation opening 152b is not communicated with the outside of nebulizer 100C. On the other hand, the first air inhalation opening 152a is communicated with flow path 101 through air inhalation valve 140. Therefore, air inhalation valve 140 is in a state capable of opening/closing the first air inhalation opening 152a utilizing pressure difference between the inner pressure of flow path 101 and the pressure outside the nebulizer 100C, and when the user inhales the aerosol, flow path 101 comes to have negative pressure and air inhalation valve 140 is pressed downward, whereby flow path 101 is communicated with the outside of nebulizer 100C. Therefore, because of the negative pressure, the external air comes to be introduced through the first air inhalation opening 152a to flow path 101.

In the second state shown in FIGS. 10A, 10B and 11B, rotating plate 192 is arranged at a position shielding the first air inhalation opening 152a. Therefore, in the second state, the first air inhalation opening 152a is in a state not communicated with the outside of nebulizer 100C. Therefore, air inhalation valve 140 does not function as a check valve. On the other hand, the second air inhalation opening 152b is in a state communicated with the outside of nebulizer 100C, and as a result, flow path 101 is communicated with the outside of nebulizer 100C through the second air inhalation opening 152b. Therefore, the second air inhalation opening 152b is always in a communicated state, and hence, when the user inhales the aerosol, flow path 101 comes to have a negative pressure and the external air is introduced through the second air inhalation opening 152b to flow path 101.

By adopting the structure described above, by a very simple operation of rotating the rotating plate on an outer surface of cap body, presence/absence of the air inhalation valve can be switched. Therefore, an appropriate amount of aerosol can be nebulized without putting a burden on the user. Further, in order to switch presence/absence of the air inhalation valve, it is unnecessary to remove only the air inhalation valve from the device body. Therefore, the air inhalation valve may not be damaged or lost. Thus, an inhaler with good handling can be provided.

As the inhaler in accordance with the present embodiment, an example having a rotating plate as the shielding section provided on an outer surface of the cap body has been described. A structure in which the rotating plate as the shielding section is provided inside the nebulizer is also possible. In that case, the rotating plate as the shielding section may be arranged on an inner surface of the case body defining the flow path or on an inner surface of the cap body.

Embodiment 4

Figure 12A:
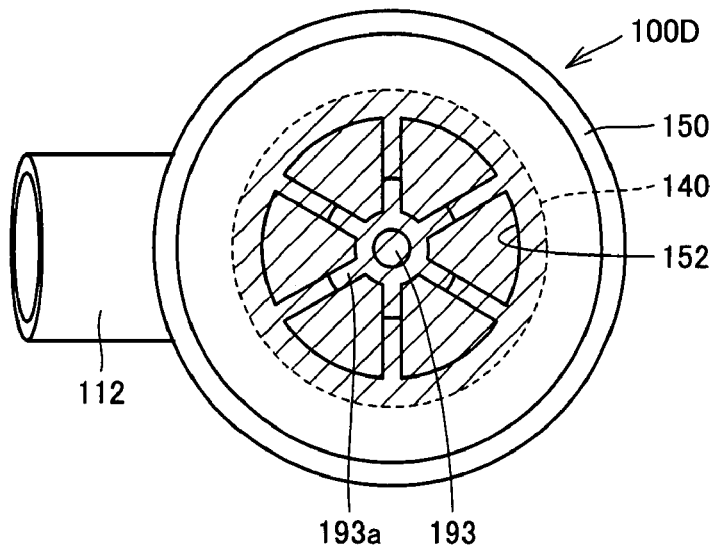
FIG. 12A is a top view of the nebulizer of the inhaler in accordance with Embodiment 4 of the present invention in the first state in which the air inhalation valve is functionable.
Figure 12B:
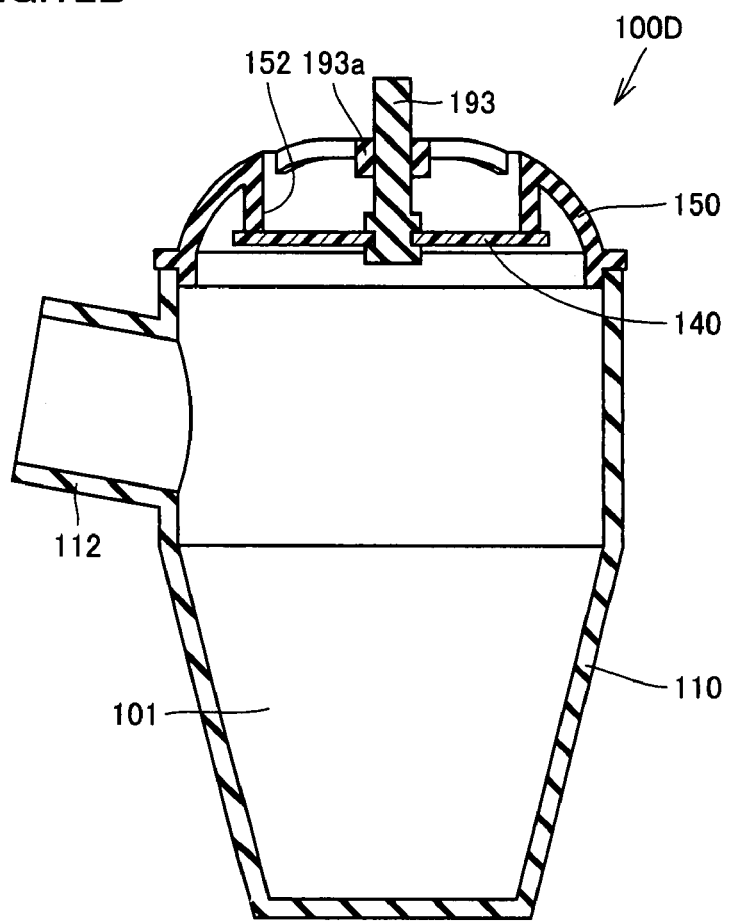
FIG. 12B is a cross-sectional view of the nebulizer of the inhaler in accordance with Embodiment 4 of the present invention in the first state in which the air inhalation valve is functionable.
Figure 13:
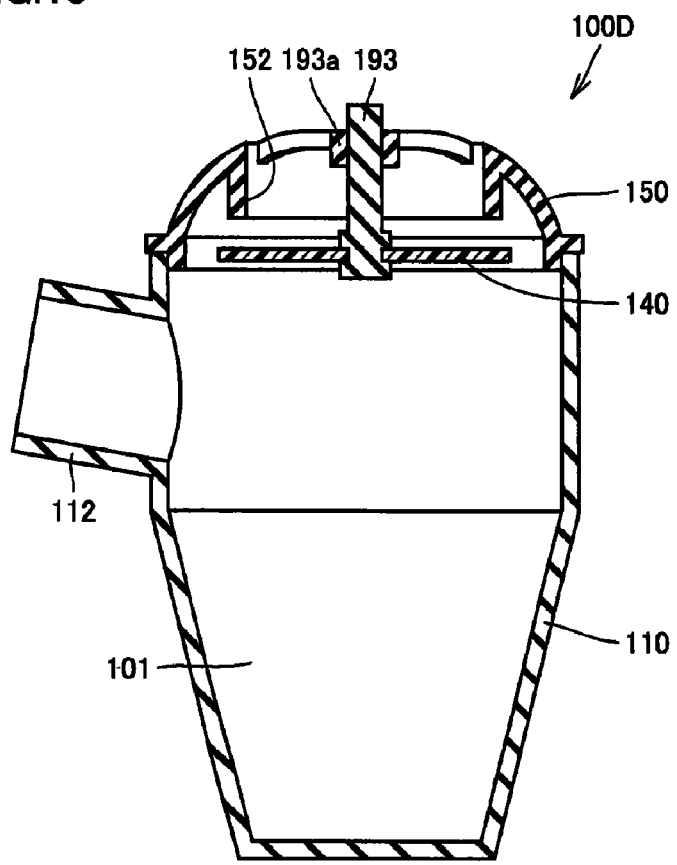
FIG. 13 is a cross-sectional view of the nebulizer of the inhaler in accordance with Embodiment 4 of the present invention in the second state in which the air inhalation valve is unfunctionable.
Figure 14:
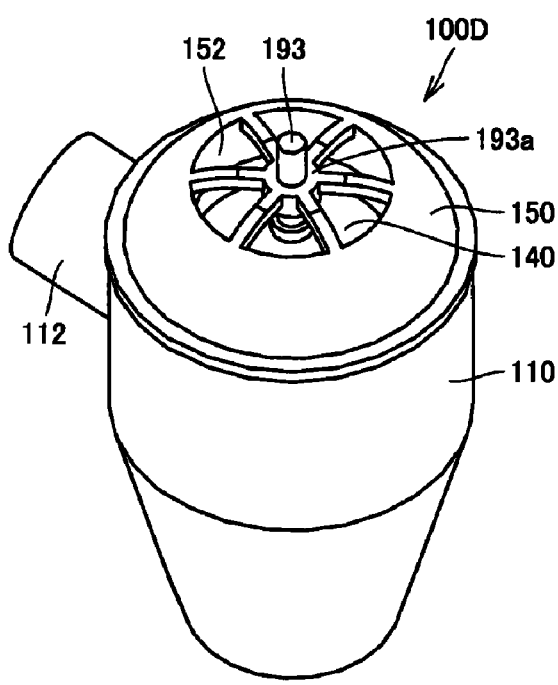
FIG. 14 is a perspective view of the nebulizer of the inhaler in accordance with Embodiment 4 of the present invention in the second state in which the air inhalation valve is unfunctionable.

FIGS. 12A and 12B are a top view and a cross-sectional view, respectively, of the nebulizer of the inhaler in accordance with Embodiment 4 of the present invention in the first state in which the air inhalation valve is functionable, and FIG. 13 is a cross-sectional view of the nebulizer of the inhaler in accordance with Embodiment 4 of the present invention in the second state in which the air inhalation valve is unfunctionable. FIG. 14 is a perspective view of the nebulizer of the inhaler in accordance with Embodiment 4 of the present invention in the second state in which the air inhalation valve is unfunctionable. In FIGS. 12A, 12B, 13 and 14, the mouthpiece is not shown, and in FIGS. 12B and 13, internal mechanism of the nebulizer is not shown. In the figures, portions similar to those of nebulizer 100A of the inhaler in accordance with Embodiment 1 are denoted by the same reference characters, and description thereof will not be repeated here.

As shown in FIGS. 12A, 12B, 13 and 14, in a nebulizer 100D of an inhaler in accordance with the present invention, an air inhalation opening 152 is provided at a prescribed position of cap body 150. Cap body 150 has a support portion 193a at its central portion, and by support portion 193a, a rod 193 as a position changing means is movably supported. At a lower end of rod 193, air inhalation valve 140 is fixed. Air inhalation valve 140 is capable of closing air inhalation opening 152, and it is a check valve for opening/closing the air inhalation opening 152 utilizing pressure difference between the inner pressure of flow path 101 and pressure outside the nebulizer 100D.

In the first state shown in FIGS. 12A and 12B, rod 193 is in a state pulled upward. In this state, air inhalation valve 140 is in a state capable of opening/closing the air inhalation opening 152 utilizing pressure difference between the inner pressure of flow path 101 and the pressure outside the nebulizer 100D, and when the user inhales the aerosol, flow path 101 comes to have negative pressure and air inhalation valve 140 is pressed downward, whereby flow path 101 is communicated with the outside of nebulizer 100D. Therefore, because of the negative pressure, the external air comes to be introduced through the air inhalation opening 152 to flow path 101.

In the second state shown in FIGS. 13 and 14, rod 193 is in a state pressed downward. In this state, air inhalation valve 140 is in a state not capable of opening/closing the air inhalation opening 152 utilizing pressure difference between the inner pressure of flow path 101 and the pressure outside the nebulizer 100D, and air inhalation valve 140 does not function as a check valve. Therefore, air inhalation opening 152 is always in a communicated state, and hence, when the user inhales the aerosol, flow path 101 comes to have a negative pressure and the external air is introduced through air inhalation opening 152 to flow path 101.

By adopting the structure described above, by a very simple operation of pulling up or pressing down the rod, presence/absence of the air inhalation valve can be switched. Therefore, an appropriate amount of aerosol can be nebulized without putting a burden on the user. Further, in order to switch presence/absence of the air inhalation valve, it is unnecessary to remove only the air inhalation valve from the device body. Therefore, the air inhalation valve may not be damaged or lost. Thus, an inhaler with good handling can be provided.

Though examples in which the present invention is applied to a compressor type inhaler have been described in Embodiments 1 to 4 above, the present invention is also applicable to an ultrasonic type inhaler or a so-called ultrasonic vibration type inhaler.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

The invention claimed is:

1. An inhaler, comprising:
   a flow path wall defining a flow path through which airflow moves, having first and second air inhalation openings for introducing external air from outside to said flow path;
   an atomizing portion provided in said flow path, for atomizing liquid reserved in a reservoir;
   a conveying portion conveying an air flow containing aerosol generated at said atomizing portion to the outside;
   an air inhalation valve attached to said flow path wall at a portion where said first air inhalation opening is provided, for opening/closing said first air inhalation opening utilizing pressure difference between said flow path and the outside; and
   a shielding section capable of selectively shielding either one of said first and second air inhalation openings; wherein
   said inhaler is structured switchable between a first state in which said second air inhalation opening is closed by said shielding section allowing introduction of external air through said first air inhalation opening utilizing said pressure difference, and a second state in which said first air inhalation opening is closed by said shielding section and communication between said flow path and the outside through said second air inhalation opening is always maintained.

2. The inhaler according to claim 1, having a case body including said flow path wall of portions not provided with said first and second air inhalation openings, and a cap body including said flow path wall of portions provided with said first and second air inhalation openings, and formed by attaching said cap body to said case body; wherein
   said shielding portion is formed by said flow path wall of the portion provided on said case body; and
   switching between said first state and said second state is made possible by changing relative position of attachment of said cap body to said case body.

3. The inhaler according to claim 1, wherein
   said shielding section is formed by a slider attached slidably on a surface of said flow path wall; and
   switching between said first state and said second state is made possible by changing relative position of said slider on the surface of said flow path wall by moving said slider.

4. The inhaler according to claim 1, wherein
   said shielding section is formed by a rotating plate attached on a surface of said flow path wall, rotatably about a rotating shaft arranged in a direction parallel to said surface; and
   switching between said first state and said second state is made possible by changing relative position of said rotating plate on the surface of said flow path wall by rotating said rotating plate.

* * * * *